(12) United States Patent
Nelson et al.

(10) Patent No.: US 12,081,944 B1
(45) Date of Patent: Sep. 3, 2024

(54) AUDIO DEVICE APPARATUS FOR HEARING IMPAIRED USERS

(71) Applicants: Clinton D. Nelson, Wauconda, IL (US); Antonius Stanciu, Timisoara (RO)

(72) Inventors: Clinton D. Nelson, Wauconda, IL (US); Antonius Stanciu, Timisoara (RO)

(*) Notice: Subject to any disclaimer, the term of this patent is extended or adjusted under 35 U.S.C. 154(b) by 0 days.

(21) Appl. No.: 18/410,655

(22) Filed: Jan. 11, 2024

Related U.S. Application Data

(63) Continuation-in-part of application No. 17/554,358, filed on Dec. 17, 2021, now abandoned.

(51) Int. Cl.
*H04R 25/00* (2006.01)
*H04R 1/10* (2006.01)

(52) U.S. Cl.
CPC ......... *H04R 25/505* (2013.01); *H04R 25/554* (2013.01); *H04R 25/558* (2013.01); *H04R 25/70* (2013.01); *H04R 1/1083* (2013.01); *H04R 2225/43* (2013.01); *H04R 2225/55* (2013.01); *H04R 2460/01* (2013.01); *H04R 2460/13* (2013.01)

(58) Field of Classification Search
CPC ............... H04R 25/505; H04R 25/554; H04R 2460/01; H04R 2205/041; H04R 5/04; H04R 1/1083
See application file for complete search history.

(56) References Cited

U.S. PATENT DOCUMENTS

| 2009/0074206 A1* | 3/2009 | Bradford | H03G 5/005 381/103 |
| 2021/0152933 A1* | 5/2021 | Boley | G06F 3/04847 |

\* cited by examiner

*Primary Examiner* — Brian Ensey
(74) *Attorney, Agent, or Firm* — Scherrer Patent & Trademark Law, P.C.; Stephen T. Scherrer; Monique A. Morneault

(57) ABSTRACT

Audio device apparatuses for hearing impaired users comprise a wearable housing connected, wired or wirelessly, to earphones or a headset. The audio device receives incoming sound, processes the incoming sound to form processed sound, and delivers the processed sound to the earphones or headset of the user.

20 Claims, 1 Drawing Sheet

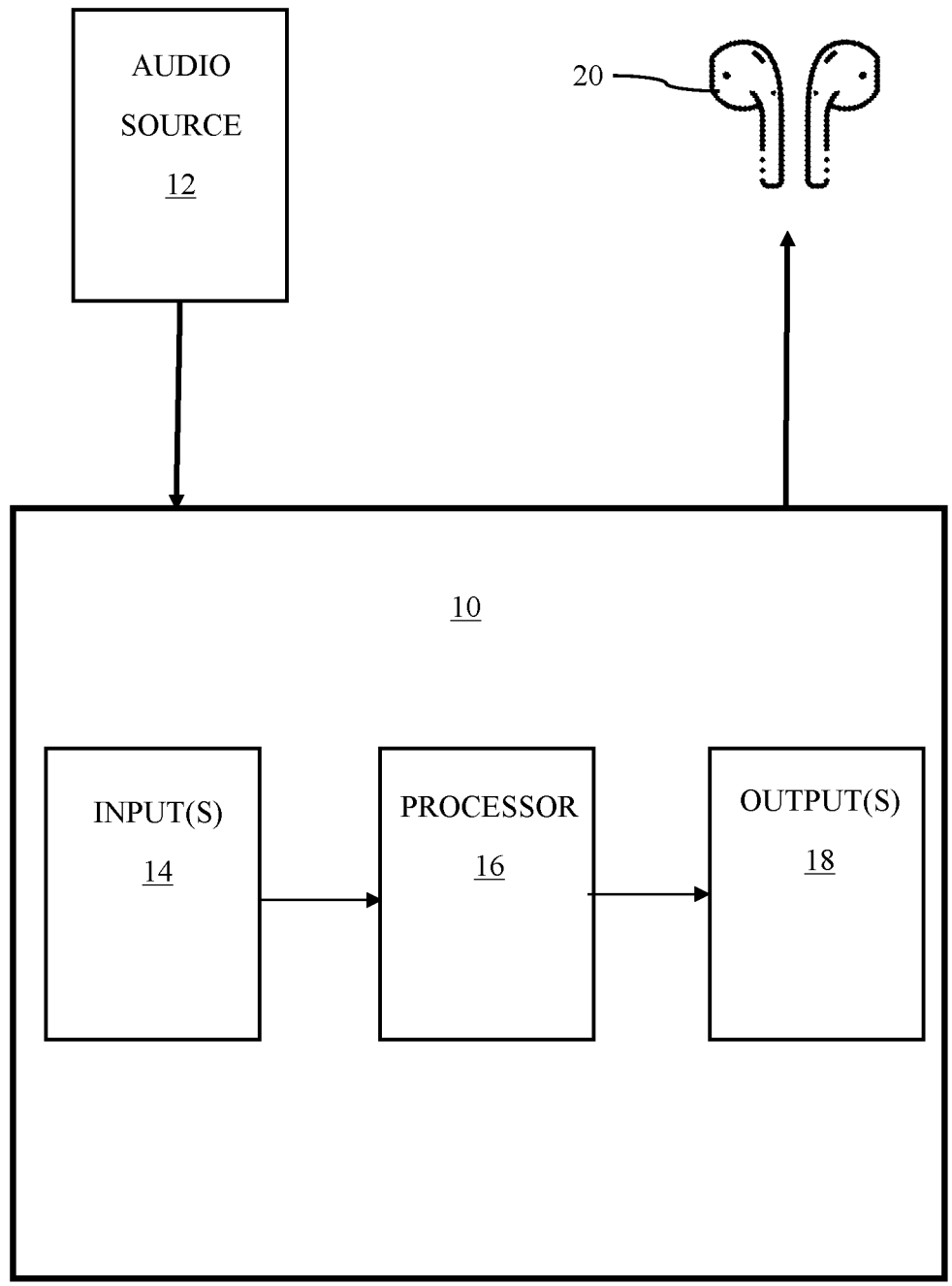

AUDIO DEVICE APPARATUS FOR HEARING IMPAIRED USERS

CROSS-REFERENCE TO RELATED APPLICATIONS

The present invention claims priority to U.S. patent application Ser. No. 17/554,358, titled "Audio Device Apparatus for Hearing Impaired Users," filed Dec. 17, 2021, which is incorporated herein by reference in its entirety.

TECHNICAL FIELD

The present invention relates to audio device apparatuses for hearing impaired users. Specifically, the audio device apparatuses comprise a wearable housing connected, wired or wirelessly, to earphones or a headset. The audio device receives incoming sound, processes the incoming sound to form processed sound, and delivers the processed sound to the earphones or headset of the user.

BACKGROUND

Hearing aids, of course, have been around for years. Early hearing aids included ear trumpets or horns that were passive amplification cones designed to capture sound energy and direct it into the ear canal. In the modern era, hearing aids are typically in-ear devices or bone conduction devices that capture audio energy and convert the same into electrical signals that are typically amplified through auditory speakers or vibrations that are directed to audio receptors within a user's ear structure.

Hearing aids are primarily difficult to utilize. The sound receptors are generally housed together with or in close proximity to the amplification modules. Oftentimes, it is difficult for a user to wear such a device in or around the ear as the housing can be relatively large. In some cases, hearing aids are worn around the ear and in some cases may be permanently attached to skull bone. Oftentimes, hearing aids are unsightly.

In other cases, because the audio receptors are often so close to audio amplification, especially via speakers, audio leakage from the speakers can be picked up by the audio receptors, causing high-pitched feedback. To ameliorate such issues, expensive sound processing can be utilized to prevent such feedback.

Moreover, because the housing holding the audio receptors and the audio speakers is often together, the audio receptors are necessarily fixed in or around the user's ear. Oftentimes, this position for receiving audio is not ideal, as sound emanating from various locations can be blocked by the user's head and is often dependent on how the user's head is positioned. Simply turning his or her head may affect the quality of audio reception.

In addition, because of the small size of hearing aids, audio processing is often minimized. Typically, the circuitry required for high quality audio processing requires larger housings to incorporate the same; therefore, many hearing aids trade size for quality, opting for smaller footprints and less audio processing. This can lead to low quality audio amplification, often not helping the user distinguish individual sounds, especially voices of others.

Hearing aids manufacturers typically tie their customers to their own solution. Usually, getting a hearing aid means performing an audiogram within a sound-proof room and, based on the audiogram, obtaining a certain type of hearing aid fitted to the supposed needs of the patient. Through an audiogram, hearing aids are typically fitted through the measurement of a single value, namely the Threshold level ("THR", which is the sound level by which patients barely begin hearing something). However, other values can be measured as well, including the "Most Comfortable Level" (MCL, which is the level a person would enjoy hearing everyday sounds at, and the "Uncomfortable Level" (UCL, which is the level at which sound becomes painful.

Typically, hearing aids are fitted to patients based only on the THR, and an average value is then used by different manufacturer's software for fitting. This may lead to poor results, causing regular noises to be unintelligible, such as, specifically, in noisy environments.

Most hearing losses are sensorineural, meaning they are nonlinear on both amplitude and frequency. In other words, hearing loss is much higher for high pitch sounds than for low pitch sounds. The tympanic membrane, which receives sound from the middle ear, does not oscillate well at high frequencies and high amplitudes, so it is very difficult to transmit heavy amplified high frequencies through the tympanic membrane to the cochlea. Therefore, many manufacturers limit the audio spectrum to about 3.5 to 4 KHz for in-ear audio devices. However, while volume sensation resides in low frequency pitches, the clarity of sounds (and mainly the clarity of speech) resides in high-pitched spectral components, which may not arrive to the cochlea with enough energy to be impactful. Moreover, when at high frequencies and high amplification, positive feedback may occur. In addition, for in-ear audio devices and hearing aids, patients often experience occlusions sensation and an increased products of cerumen inside the ear canal.

A need, therefore, exists for improved audio device apparatuses. Specifically, a need exists for improved audio device apparatuses that are easy to wear and use. More specifically, a need exists for improved audio device apparatuses having earphones, earbuds or headsets that are small and generally unnoticeable, and remain relatively unseen by others.

Moreover, a need exists for improved audio device apparatuses that generally divide the audio receptors from the audio speakers. Specifically, a need exists for improved audio device apparatuses that minimize or eliminate feedback issues.

In addition, a need exists for improved audio device apparatuses that provide better positioning of audio receptors. Specifically, a need exists for improved audio device apparatuses that allow for reception of audio without being beholden to a user's head position.

Further, a need exists for improved audio device apparatuses having high quality audio processing technology. Specifically, a need exists for improved audio device apparatuses allowing for the ability for a user to easily distinguish certain sounds and, especially, human voices.

SUMMARY OF THE INVENTION

The present invention relates to audio device apparatuses for hearing impaired users. Specifically, the audio device apparatuses comprise a wearable housing connected, wired or wirelessly, to earphones or a headset. The audio device receives incoming sound, processes the incoming sound to form processed sound, and delivers the processed sound to the earphones or headset of the user.

To this end, in an embodiment of the present invention, an audio device apparatus is provided. The audio device apparatus comprises: a plurality of inputs, wherein each of the plurality of inputs is configured to receive an audio signal; a processor, wherein the processor processes the audio signal to form a processed audio signal; and a plurality of outputs, wherein at least one of the plurality of outputs sends a wireless signal to a headset, wherein the headset plays the processed audio signal.

In an embodiment, one of the plurality of inputs is a line-in port.

In an embodiment, the line-in port is a TOS link optical input port.

In an embodiment, one of the plurality of inputs is a microphone.

In an embodiment, one of the plurality of inputs is a wireless receiver.

In an embodiment, the wireless receiver is configured to receive a Bluetooth signal.

In an embodiment, the processor converts a received analog audio signal into a digital audio signal.

In an embodiment, the processor comprises an adjustable graphic equalizer.

In an embodiment, the processor is configured to apply noise cancelling to the digital analog signal.

In an embodiment, the processor is configured to apply transient noise suppression to the digital audio signal.

In an embodiment, one of the plurality of outputs comprises a line-out port.

In an embodiment, the line-out port comprises a TOS link optical output port.

In an embodiment, the headset comprises earbuds.

In an embodiment, the headset is bone conducting.

In an embodiment, the processor identifies one or more human voices within the digital audio signal.

In an embodiment, the processor enhances the one or more human voices within the digital audio signal.

In an embodiment, the processor reduces ambient noise relative to the one or more human voices within the digital audio signal.

In an alternate embodiment, a method of enhancing audio signals is provided. The method comprises the steps of: providing the audio device apparatus; receiving an audio signal via one or more of the plurality of inputs of the audio device apparatus; processing the audio signal into a processed audio signal via the processor of the audio device apparatus; and outputting the processed audio signal via one or more of the plurality of outputs.

In an embodiment, the method further comprising the steps of: conducting a hearing test on a patient and generating an audiogram showing patient hearing loss; and adjusting the processor to optimize the processed audio signal for the patient.

In an embodiment, the processor utilizes a graphic equalizer for automatically adjusting the audio signal based on the patient's audiogram.

It is, therefore, an advantage and objective of the present invention to provide improved audio device apparatuses.

Specifically, it is an advantage and objective of the present invention to provide improved audio device apparatuses that are easy to wear and use.

More specifically, it is an advantage and objective of the present invention to provide improved audio device apparatuses having earphones, earbuds or headsets that are small and generally unnoticeable, and remain relatively unseen by others.

Moreover, it is an advantage and objective of the present invention to provide improved audio device apparatuses that generally divide the audio receptors from the audio speakers.

Specifically, it is an advantage and objective of the present invention to provide improved audio device apparatuses that minimize or eliminate feedback issues.

In addition, it is an advantage and objective of the present invention to provide improved audio device apparatuses that provide better positioning of audio receptors.

Specifically, it is an advantage and objective of the present invention to provide improved audio device apparatuses that allow for reception of audio without being beholden to a user's head position.

Further, it is an advantage and objective of the present invention to provide improved audio device apparatuses having high quality audio processing technology.

Specifically, it is an advantage and objective of the present invention to provide improved audio device apparatuses allowing for the ability for a user to easily distinguish certain sounds and, especially, human voices.

Additional features and advantages of the present invention are described in, and will be apparent from, the detailed description of the presently preferred embodiments and from the drawings.

BRIEF DESCRIPTION OF THE DRAWINGS

The drawing FIGURES depict one or more implementations in accord with the present concepts, by way of example only, not by way of limitations. In the FIGURES, like reference numerals refer to the same or similar elements.

FIG. 1 illustrates a diagram of an audio device apparatus in an embodiment of the present invention.

DETAILED DESCRIPTION OF THE PRESENTLY PREFERRED EMBODIMENTS

The present invention relates to audio device apparatuses for hearing impaired users. Specifically, the audio device apparatuses comprise a wearable housing connected, wired or wirelessly, to earphones or a headset. The audio device receives incoming sound, processes the incoming sound to form processed sound, and delivers the processed sound to the earphones or headset of the user.

Now referring to the FIGURES, wherein like numerals refer to like parts, FIG. 1 illustrates a diagram showing an audio device apparatus 10 in accordance with the present invention. Specifically, the audio device apparatus 10 comprises inputs 14, a processor 16, and outputs 18. Generally, an audio source 12, which may be sound waves generated by a source, such as a person's voice, or other like source, or may be electrical signals carrying analog or digital audio signals therein, may be received via the inputs 14. Specifically, the audio device apparatus 10 may have several inputs 14, including wireless receiver technology for receiving wireless signals, such as Bluetooth signals or the like. Moreover, inputs 14 may include a line-in port, such that electrical audio signals may be received directly by the audio device apparatus 10. A specific line-in port may be a TOS link optical port for receiving optical signals. In addition, inputs 14 may include a microphone for detecting ambient sound waves.

Audio signals received by the audio device apparatus 10 may be processed via the processor 16. First, if the audio signals are received in analog form, the processor 16 may convert the same to digital format. Once in digital format, the processor may process the digital audio signal and amplify the same. Specifically, the digital audio signal may be analyzed to identify human voice elements, and the human voice elements may be enhanced via processing, specifically by isolating the human voice elements and reducing other ambient noise that may be received. In addition, the audio signal may be enhanced by distinguishing elements thereof by direction. Specifically, audio may be identified as coming from a particular direction and enhanced as such to be more easily distinguished by a user thereof. More specifically, audio coming from right and left of the user may be distinguished by timbre and/or tone. Moreover, to further enhance audio from different directions, audio signals may be delayed from either left or right for a specific channel. As such, the processor 16 may include a graphic equalizer, noise cancelling processing and transient noise suppression, and/or other like processing means.

The processing means may be adjustable such that they may be specifically tuned to a user's needs. For example, a user may be tested, and an audiogram may be generated, whereby the audiogram may be utilized to adjust the processing means for optimization of the digital audio signal, as desired. Preferably, the audiogram may be entered into the processor, and the processor may automatically adjust the audio signal to optimize the same based on the needs and requirements of the user.

Preferably, in the present invention, three data points are utilized to finetune processing of audio signals. Specifically, as normal, a THR value is measured, which is the level at which a person can just barely begin to hear something. Likewise, an MCL value is measured, which is the level at which a person is most comfortable listening to audio signals. Finally, a UCL value is measured, which is the level at which sound becomes painful to an individual. Based on these three measured values, the processing means within the smartphone may process the input audio signal and automatically adjust the same to optimize the same for a user.

Moreover, the audio may be processed into a visual representation that may be seen by a user. For example, audio received by the present system may be processed and displayed by a representation of a human mouth thereby allowing lip reading by the user. Alternatively, the audio may be processed into text that may be read by a user. A display may be incorporated into the present invention and the user may be see the audio represented in a visual form on the display. The display may be a screen, such as on the user's smartphone, or on a wearable visual display such as Google Glass™ wearable display glasses.

Once processed, the digital audio signal may be sent to one or more of multiple outputs 18. In a preferred embodiment, the outputs 18 may include ear buds 20, or earphones, headphones, a headset, such as a bone conduction headset, or other like audio generating element worn near or in the user's ear. The ear buds 20 may be wired or wireless, such as via Bluetooth, to receive the processed digital audio signal and play the same into the user's ear. In a most preferred embodiment, the outputs 18 may be a bone conduction headset, due to the ability of bone conduction headsets to send sound as a mechanical vibration through the temporal bone directly to the cochlea, thereby completely circumventing the middle ear and the tympanic membrane. As a result, sound waves may be generated over a full spectrum, including high frequencies, such as between 125 Hz to up to 8 KHz, which may then be delivered directly to the cochlea through the temporal bone. Preferably, the audio device of the present invention outputs signals above about 4 KHz, more preferably above about 5 KHz, more preferably above about 6 KHz, and more preferably above about 7 KHz. Therefore, wearers of the bone conduction headsets in the present invention may obtain better clarity and intelligibility in sounds and an open ear canal, preventing occlusions and cerumen buildup.

Alternatively, the processed digital audio signal may be output via a line-out, so that the same may be played by an external speaker, such as a sound bar, or other like speaker device. The line-out may be a TOS link optical output. As previously noted, the processed audio signal may be sent to a display and processed into a form that may be viewable by a user, such as a mouth for lipreading and/or text for reading.

The present invention may be in the form of a software application and may be resident and utilized on a smartphone, for example. Specifically, the smartphone may be the audio device apparatus 10, including multiple inputs and a microphone. The software application may provide the required processing means as described herein. Moreover, the smartphone may further have multiple outputs, as described above.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

We claim:

1. An audio device apparatus comprising:
a smartphone having a software application disposed thereon, the smartphone comprising a plurality of inputs, wherein each of the plurality of inputs is configured to receive an audio signal, a processor, wherein the processor processes the audio signal to form a processed audio signal, and at least one audio output, where the at least one audio output sends a wireless signal to a bone conduction headset, wherein the bone conduction headset is configured to play the processed audio signal,
wherein the software application generates an audiogram measuring hearing loss by testing a user via the headset and further wherein the processed signal sent to the headset is adjusted based on the audiogram,
wherein the testing of the user via the headset measures a threshold (THR) level, wherein the user inputs to the smartphone a first spectral value where the user barely hears an audio signal, a most comfortable level, where the user inputs to the smartphone a second spectral value where the user is most comfortable receiving audio signals, and an uncomfortable level, where the user inputs to the smartphone a third spectral value where the user becomes uncomfortable receiving audio signals,
wherein the processed signal sent to the bone conduction headset is processed based on the first, second, and third spectral values, and further wherein the processed signal includes frequencies above about 4 KHz.

2. The audio device apparatus of claim 1 wherein one of the plurality of inputs is a line-in port.

3. The audio device apparatus of claim 2 wherein the line-in port is a TOS link optical input port.

4. The audio device apparatus of claim 1 where one of the plurality of inputs is a microphone.

5. The audio device apparatus of claim 1 wherein one of the plurality of inputs is a wireless receiver.

6. The audio device apparatus of claim 5 wherein the wireless receiver is configured to receive a Bluetooth signal.

7. The audio device apparatus of claim 1 wherein the processor converts a received analog audio signal into a digital audio signal.

8. The audio device apparatus of claim 1 wherein the processor comprises an adjustable graphic equalizer.

9. The audio device apparatus of claim 1 wherein the processor is configured to apply noise cancelling to the digital analog signal.

10. The audio device apparatus of claim 1 wherein the processor is configured to apply transient noise suppression to the digital audio signal.

11. The audio device apparatus of claim 1 wherein one of the plurality of outputs comprises a line-out port.

12. The audio device apparatus of claim 11 wherein the line-out port comprises a TOS link optical output port.

13. The audio device apparatus of claim 1 wherein the headset is selected from the group of earbuds and a bone conducting headset.

14. The audio device apparatus of claim 1 further comprising a display configured to display a visual representation of the audio signal.

15. The audio device apparatus of claim 1 wherein the processor identifies one or more human voices within the digital audio signal.

16. The audio device apparatus of claim 15 wherein the processor enhances the one or more human voices within the digital audio signal.

17. The audio device apparatus of claim 15 wherein the processor reduces ambient noise relative to the one or more human voices within the digital audio signal.

18. A method of enhancing audio signals comprising the steps of:
providing the audio device apparatus of claim 1;
receiving an audio signal via one or more of the plurality of inputs of the audio device apparatus;
processing the audio signal into a processed audio signal via the processor of the audio device apparatus, wherein the processing is based on the first, second, and third spectral values; and
outputting the processed audio signal to the bone conduction headset.

19. The method of claim 18 further comprising the steps of:
conducting a hearing test on a patient and generating an audiogram showing patient hearing loss based on the first, second, and third spectral values; and
adjusting the processor to optimize the processed audio signal for the patient.

20. The method of claim 19 wherein the processor utilizes a graphic equalizer for automatically adjusting the audio signal based on the patient's audiogram.

* * * * *